(12) United States Patent
Gu et al.

(10) Patent No.: US 8,708,496 B2
(45) Date of Patent: Apr. 29, 2014

(54) METHODS FOR IMAGING OCULAR DEVICES USING OPTICAL COHERENCE TOMOGRAPHY

(75) Inventors: Yeming Gu, Suwanee, GA (US); Rebeca Kyker Bowden, Athens, GA (US); William Jordan Hall, Atlanta, GA (US); Deborah J. Mulcahy, Suwanee, GA (US); Yongxing Qiu, Duluth, GA (US); Benjamin David Sullivan, Duluth, GA (US); Robert Carey Tucker, Suwanee, GA (US)

(73) Assignee: Novartis AG, Basel (CH)

( * ) Notice: Subject to any disclaimer, the term of this patent is extended or adjusted under 35 U.S.C. 154(b) by 253 days.

(21) Appl. No.: 13/207,171

(22) Filed: Aug. 10, 2011

(65) Prior Publication Data

US 2012/0038888 A1    Feb. 16, 2012

Related U.S. Application Data

(60) Provisional application No. 61/372,730, filed on Aug. 11, 2010.

(51) Int. Cl.
*A61B 3/00* (2006.01)
*A61B 3/10* (2006.01)

(52) U.S. Cl.
CPC .................................... *A61B 3/102* (2013.01)
USPC .......................................... 351/246; 351/247

(58) Field of Classification Search
CPC .............................. A61B 3/1225; A61B 3/102
USPC .................. 351/205, 210, 216, 221, 246, 247
See application file for complete search history.

(56) References Cited

U.S. PATENT DOCUMENTS

| | | | |
|---|---|---|---|
| 7,198,777 B2 | 4/2007 | Boppart et al. | |
| 2006/0285635 A1* | 12/2006 | Boppart et al. | 378/22 |
| 2007/0195311 A1 | 8/2007 | Morgan et al. | |
| 2007/0286468 A1 | 12/2007 | Joshi et al. | |

FOREIGN PATENT DOCUMENTS

WO        2009058850 A1    5/2009

OTHER PUBLICATIONS

Authors: Anant Agrawal, Stanley Huang, Joshua Pfefer, Min-Ho Lee, Rebekah Drezek Title: Quantitative Evaluation of Nanoshells as a Contrast Agent for Optical Coherence Tomography Published: 2005 Optical Society of America, 2005 Conference on Lasers & Electro-Optics, pp. 2049-2051.

Authors: Chenyang Xu, Jian Ye, Daniel L. Marks, Stephen a. Boppart Title: Near-Infrared Dyes as Contrast-Enhancing Agents for Spectroscopic Optical Coherence Tomography Published: 2004 Optical Society of America, Jul. 15, 2001, vol. 29, No. 14, Optics Letters, pp. 1647-1649.

Author: Stephen A. Boppart Title: Advances in Contrast Enhancement for Optical Coherence Tomography Published: Engineering in Medicine and Biology Society, 2006, 28th IEEE EMBS Annual International Conference New York City, NY, Aug. 30-Sep. 3, 2006, pp. 121-124.

* cited by examiner

*Primary Examiner* — Huy K Mai
(74) *Attorney, Agent, or Firm* — Robert Ambrose

(57) ABSTRACT

Described herein are methods for imaging ocular devices. The methods generally involve (a) applying a scattering agent to the ocular device; and (b) imaging the ocular device using optical coherence tomography (OCT). The methods described herein provide useful structural information about the surface of the device with high sensitivity.

13 Claims, 8 Drawing Sheets

METHODS FOR IMAGING OCULAR DEVICES USING OPTICAL COHERENCE TOMOGRAPHY

This application claims the benefit under 35 USC §119 (e) of U.S. provisional application Ser. No. 61/372,730 filed on Aug. 11, 2010, incorporated herein by reference in its entirety.

BACKGROUND

Optical Coherence Tomography (OCT) is a fast-growing imaging technique that has found wide application especially in the biomedical field. OCT, including SS-OCT ("swept source OCT") performs high resolution, cross sectional imaging in semitransparent samples (such as biological tissues, etc.) by measuring the echo time delay of reflected light. OCT can also be used to create 3-D images by combining 2-D cross-section images. For example, OCT has been used to image biotissue samples and has many applications ranging from intravascular imaging to cancer diagnosis.

OCT has had a major impact in ophthalmology and metrology. However, one important challenge in using OCT images for metrology applications is obtaining an adequate signal to noise ratio (S/N) of the OCT image to enable accurate measurement of image features, such as the profile of the sample or sample components.

SUMMARY

Described herein are methods for imaging ocular devices such as, for example, contact lenses and intraocular lenses. The methods described herein provide useful structural information about the surface of the device with high sensitivity. The methods generally involve (a) applying a scattering agent to the ocular device; and (b) imaging the ocular device using optical coherence tomography (OCT). In embodiments, the application of the scattering agent may be accomplished by submerging the ocular device in a solution including the scattering agent. The ocular device may be imaged in liquids, for example in water, saline, or a buffered solution, and/or be imaged in a solution of scattering agent. The ocular device may be imaged, for example, by use of a Frequency Domain OCT, Fourier-domain OCT (FDOCT), complex Fourier OCT, Optical Frequency-domain imaging, or swept-source OCT.

In exemplary embodiments, the scattering agent can be or include one or more pigments, such as for example Green Cr2O3, Yellow Iron Oxide, combinations thereof. The pigment can be or include a water-insoluble salt that forms in situ on the surface of the ocular device, throughout the device, or a combination thereof, and the water-insoluble salt may, for example, be or include a silver salt.

In other embodiments, the imagine method may include such additional steps following step (a) and prior to step (b) such as the steps of (i) rinsing the ocular device and (ii) submerging the ocular device in a solution of water, saline, or a buffered solution.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

DETAILED DESCRIPTION

Figure 1:
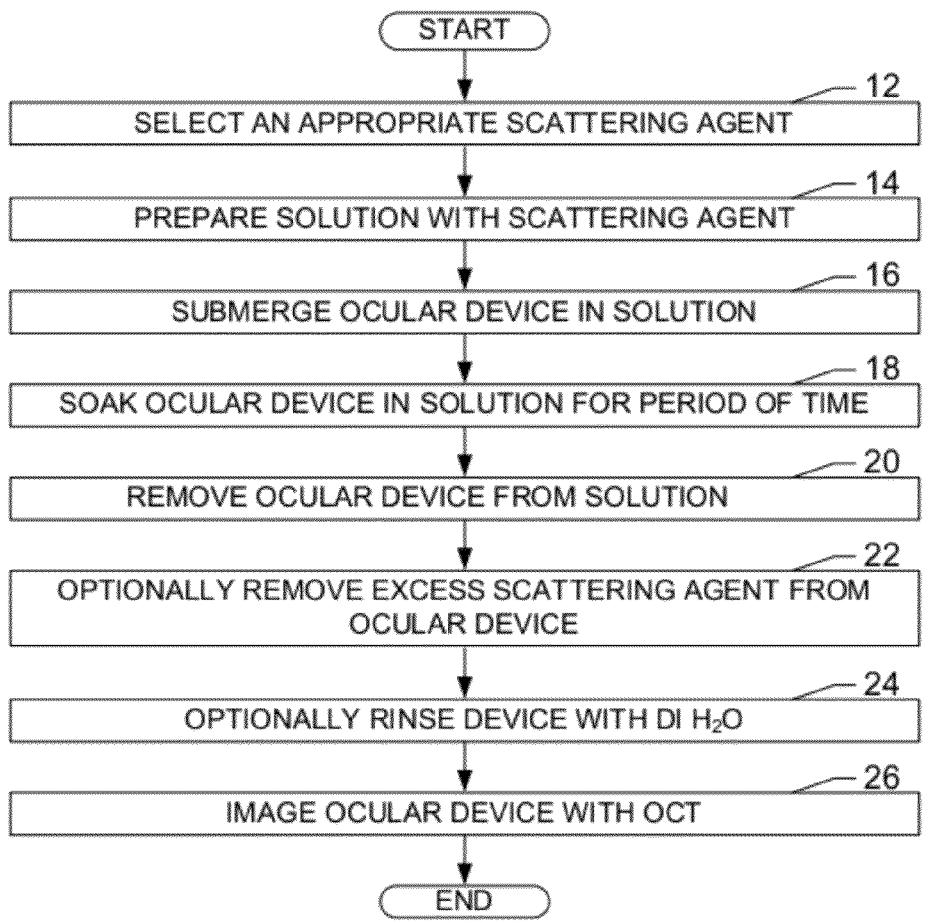
FIG. 1 is a flow diagram of an exemplary method described herein for imaging an ocular device using OCT.

The methods described herein may be understood more readily by reference to the following detailed description taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Described herein are methods for imaging ocular devices. Examples of ocular devices useful herein include, but are not limited to, contact lens and intraocular lenses. The methods generally involve (a) applying a scattering agent to the ocular device; and (b) imaging the ocular device using optical coherence tomography (OCT). Each step is described in detail below.

The first step involves applying a scattering agent to the ocular device. Not wishing to be bound by theory, the scattering agent increases the number of light scattering sites on the device, which in turn increases the signal-to-noise ratio when the device is imaged by OCT. By increasing the signal-to-noise ratio, the methods described herein provide greater sensitivity with respect to imaging the surface of the device. This is shown in the Examples below.

A variety of different compounds can be used as the scattering agent. The selection of the scattering agent can be based on variables such as particle size and the resulting scattering efficiency for the wavelength range of the corresponding OCT light source. Different scattering agents are likely to be used with different wavelength ranges. The selection of the scattering agent can also be based on the application setup. For example, when a contact lens is imaged in solution, the scattering agent particles are fairly small (e.g., less than 1 micron in diameter) and are able to stick to the surface of the sample (see below).

In one aspect, the scattering agent is a dye. In general, the dyes useful herein are water-soluble compounds. For example, the dyes are soluble in saline or buffered solutions. Examples of dyes useful herein include, but are not limited to, potassium tri-iodide, Indocyanine Green, fluorescein, SNARF, Rose Bengal, Fura Red, or any combination thereof. The selection of the dye can depend upon, among other things, the color of the selected dye and the working wavelength of the OCT instrument.

In other aspects, the scattering agent is or includes one or more pigments. The pigments useful herein are generally solid particles that can be deposited on the surface of the ocular device and/or throughout the ocular device. In certain aspects, when the pigment is added to an aqueous solution, the pigment is a fine suspension of solid particles. For example, Green $Cr_2O_3$ and Yellow Iron Oxide when added to water is a suspension of solid particles. In this aspect, this approach is useful in depositing the pigment on the surface of the ocular device.

In other aspects, the pigment is formed in situ while the device is in an aqueous solution including a pigment precursor. In one aspect, the pigment precursor can be a water-soluble salt such as a silver salt. When the silver salt interacts with the chloride ions present in the saline solution, silver chloride and/or silver phosphate are produced as solid particles (i.e., the pigment). Other silver salts such as, for example, silver acetate or silver citrate, can also be used as pigment precursors. In this aspect, the pigment can be deposited on the surface of the device, incorporated throughout the device, or a combination thereof. In the case when the ocular device is a porous material, the water-soluble salt can penetrate the pores of the device and subsequently be converted to an insoluble salt (i.e., pigment) within the device. For example, silicon hydrogel contact lenses have a significant amount of saline incorporated within the lens, which can react with silver salts to produce silver chloride and/or silver phosphate pigment throughout the lens. By increasing the amount of pigment throughout the device, it is possible to achieve greater sensitivity when imaging with OCT. Exemplary methods for producing silver pigment in situ are provided in the Examples.

In other aspects, the scattering agent can include other materials such as, for example, protein microspheres, microbeads and nanoparticles. Protein microspheres have an exterior protein shell and an interior containing a gas, a liquid or particles. The compositions of the shell and the interior may be varied to produce microspheres having different spectral scattering properties. The spectral scattering properties may also be affected by the relative dimensions of the shell and the interior. In certain aspects, the protein in the exterior shell can also be engineered such that melanin, gold or carbon particles are embedded.

Simple microbeads having sizes close to the selected laser wavelength can provide Mie scattering of the laser radiation. The spectral scattering can be further modified by coating the beads with dye as described herein or other materials.

Metal nanoparticle scattering agents can be solid particles or can be nanoshells. Solid metal nanoparticles can be formed in a variety of shapes, which can affect the optical scattering properties. Metal nanoshells can have a core containing a dielectric material, and modifications in the shape, composition and relative dimensions of core and the shell can provide for systematic variation of the optical resonance over a broad wavelength region, ranging from near-UV to the mid-infrared. Gold nanoshells can be engineered to scatter or absorb light primarily in the wavelength ranges typically used for OCT.

Once the scattering agent has been applied to the ocular device, the device is imaged using OCT. OCT is a method for noncontact optical imaging that takes advantage of sequential or scanned distance measurements. In biological and biomedical imaging applications, OCT allows for micrometer-scale imaging noninvasively in transparent and translucent biological tissues. The interference pattern of light reflected or backscattered from the sample and light from the reference delay contains information about the location and scattering amplitude of the scatterers in the sample. In conventional (time-domain) OCT, this information is extracted by scanning the reference path delay and detecting the resulting interference signal as a function of that delay. Although useful in bioimaging applications, OCT is limited in metrology applications due to low signal-to-noise ratio of the OCT image. The use of scattering agents described herein addresses this shortcoming and permits high sensitivity imaging of ocular devices. In one aspect, the ocular device can be imaged by Frequency Domain OCT or Fourier-domain OCT (FDOCT), complex Fourier OCT, Optical Frequency-domain imaging, or swept-source OCT.

FIG. 1 shows a flow diagram of an exemplary method 10 of imaging an ocular device using OCT. Referring to FIG. 1, the method begins at step 12 when an appropriate scattering agent is selected. Once the scattering agent is selected, an aqueous solution including an appropriate concentration of the scattering agent is prepared at step 14. The aqueous solution can include any aqueous solution including, but not limited to, water, deionized water, saline, buffered saline (e.g., phosphate buffered saline or PBS), or any combination thereof. The ocular device is then submerged in the solution containing the scattering agent (steps 16 and 18).

The ocular device is then removed from the solution at step 20, and excess scattering agent can optionally be removed from the device at step 22. The excess scattering agent can be removed by gently shaking the device and touching the device edge and front curve with a dry tissue. Optionally, the device can be further rinsed with deionized water at step 24 by soaking the device in deionized water in order to remove additional scattering agent.

Once the scattering agent has been applied to the device, the device is imaged using OCT technology at step 26. Although not shown in FIG. 1, the device can be imaged in either a transparent solution (e.g., water, saline, etc.), in a solution of scattering agent, or in air. The OCT image can provide valuable information regarding certain geometric features of the ocular device. For example, geometric properties such as shape of the front curve and base curve can be obtained. Additionally, the thickness of the device as calculated by the distance between the front curve and base curve of the device can also be obtained.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is as-stated in ° C. or is at ambient temperature, and pressure is at or near atmospheric.

Example 1

Evaluation of Nelfilcon Pigments

CIBA VISION® FRESHLOOK® lenses, made of Phemfilcon A, include a printed pattern that appears brightly on an SS-OCT image, which thus makes it difficult to view surface edges. A previous test was conducted using both a fluorescent dye and a Rose Bengal dye. However, neither of these appeared to enhance the signal of the lens. Eight Nelfilcon pigments were obtained to further test this theory. All images in this example were taken at 0-30 dB and the brightness and contrast of all images were left at the default value of 50%.

First, a small amount of each of the eight Nelfilcon pigments was diluted with PBS saline and was imaged in an open-top, plastic dish, about 3-4 mm deep. The eight Nelfilcon dyes included Green $Cr_2O_3$ GR-3188-24B, Black I.O. Bk-4061-84A, Blue Oxide BLO-3188-45A, Black 3226-50, Yellow I.O. YW-3226-65, White $TiO_2$ WH-3188-27A, Red I.O. RD-3188-63A, and PCN Blue BL-3020-30A.

Based on the images obtained, Green $Cr_2O_3$ and Yellow Iron Oxide provided the best results because these possess a good signal all the way to the bottom of the dish and the two lines of the bottom of the dish are still clearly visible.

Example 2

Imaging Clean Lenses in Diluted Pigment

Figure 2A:
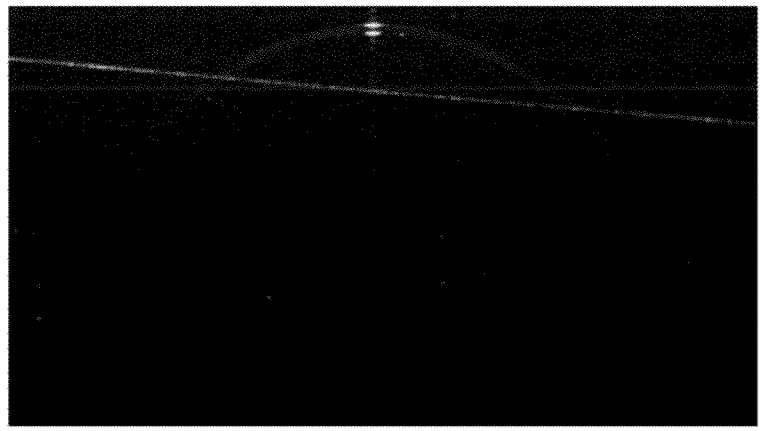
FIG. 2 shows an OCT image of a DAILIES® sphere lens with Yellow Iron Oxide and Green $Cr_2O_3$.
Figure 2B:
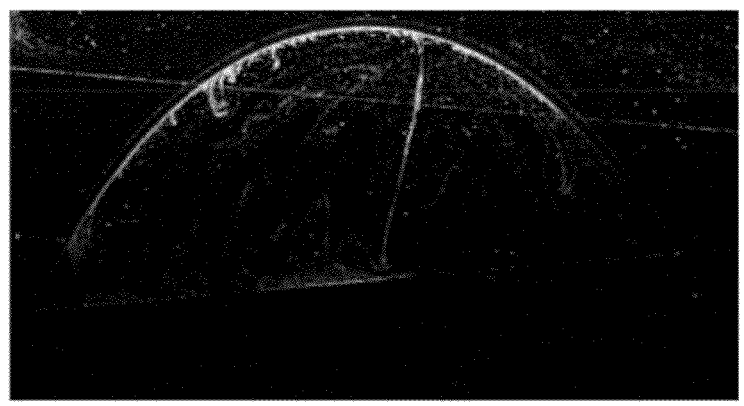
Figure 2C:
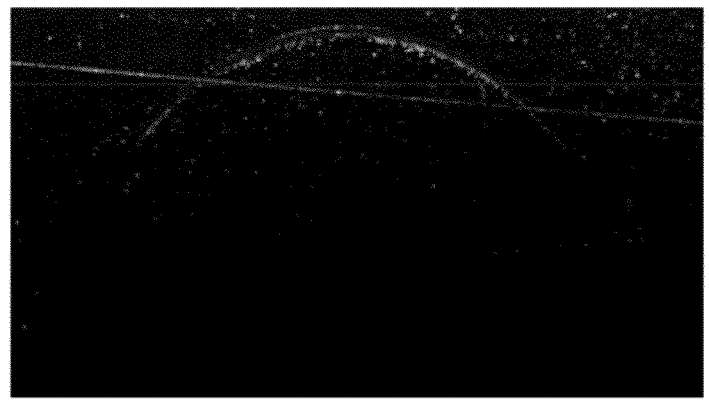
Figure 3A:
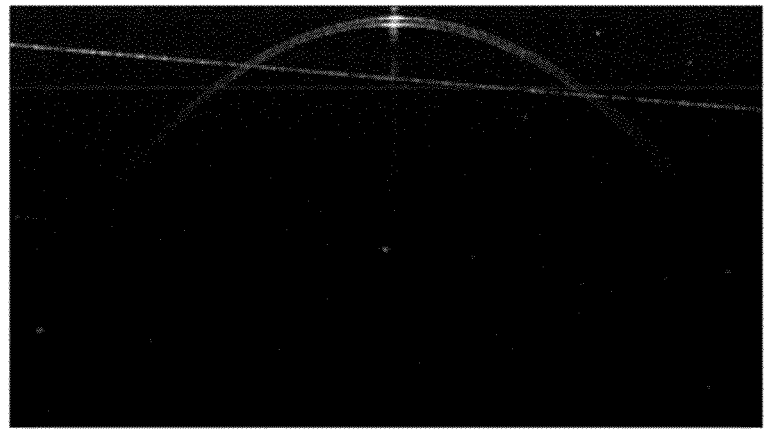
FIG. 3 shows an OCT image of an O2OPTIX® sphere lens with Yellow Iron Oxide and Green $Cr_2O_3$.
Figure 3B:
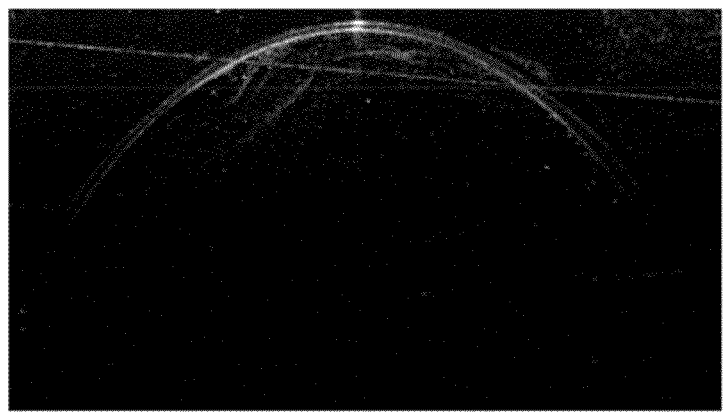
Figure 3C:
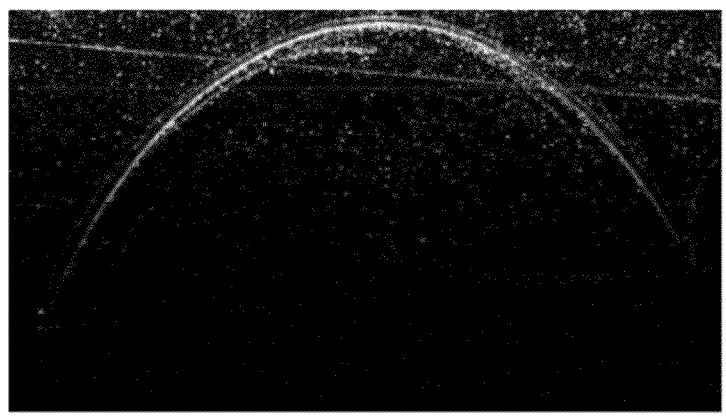

A DAILIES® sphere lens (made of Nelfilcon A, a PVA) and an O2OPTIX® sphere lens (made of lotrafilcon B, a silicone hydrogel material) were each imaged in solutions of the green and yellow Nelfilcon pigments diluted with PBS saline (FIGS. 2 and 3, respectively). The lenses were then imaged with OCT technology. In these images, the lenses can be seen because the solution is tinted and has signal, but the lenses do not. All images were taken with the lenses in wetcells. After comparing the images of the DAILIES® lens in the yellow and green pigments, it appeared that the yellow pigment produced signal through a greater depth than the green pigments (FIG. 2B). Conversely, the green pigment produced a better signal with the O2OPTIX® sphere lens (FIG. 3C).

Example 3

Imaging Lenses in Clean Saline

Two DAILIES® and two O2OPTIX® lenses were allowed to soak in vials of saline-diluted Nelfilcon pigment (one of each in green and one of each in yellow) for a little over four hours. Then, each lens was quickly rinsed in clean saline and placed in a wetcell containing clean saline. Also, a clean lens of each type (from the same lots as the others) was imaged for comparison.

Both pigments do improve the signal of the lens edge. The yellow pigment appeared to stick to the lens better than the green pigment. However, the yellow pigment can be seen separating from the lens and mixing with the saline. The base curves of the lenses appeared more brightly than the front curves. It is likely that this is due to the lenses sitting base-curve-up in the vials, causing pigment to accumulate more on the base curve. The pigment also separated from the lenses as well.

Example 4

Lotrafilcon A Lenses with Silver Salt/Pigment

Several CIBA VISION® NIGTHT & DAY® contact lenses (made of lotrafilcon A, a silicone hydrogel material) were tested in a silver nitrate ($AgNO_3$) solution. Twenty five groups of lenses were tested. Each group included three lenses, and five different concentrations (wt %) of Ag $NO_3$ solution were tested. The three lenses for each group were prepared in 5 ml of PBS (phosphate buffered saline). Diameter, center thickness, and base curve were measured for each lens.

Five aqueous $AgNO_3$ stock solutions, each 750 ml and comprising a different concentration of $AgNO_3$, were prepared. The $AgNO_3$ concentrations included 0.01 wt %, 0.02 wt %, 0.04 wt %, 0.08 wt %, and 0.16 wt %. Each stock solution was divided in equal parts (150 ml) and placed into a beaker. Thus, there were five beakers of each stock solution. Each concentration of $AgNO_3$ was tested for five different soak times. Soak times included 5 sec., 10 sec., 15 sec., 20 sec., and 30 sec.

A magnetic stir bar was placed into each beaker. A separate beaker was filled with 150 ml of deionized water (DI $H_2O$) from house DI $H_2O$ supply, and a magnetic stir bar was added to that beaker. The first beaker of 150 ml of $AgNO_3$ coating solution was placed onto a stir plate and stirring action was maintained. The stir plate model and speed settings were recorded. A new contact lens was removed from its vial and excess saline was removed by gently shaking the lens and touching the lens edge and front curve to dry tissue. The lens was soaked for the specified time as indicated in Table 1, and the lens was rotated 180 degrees halfway through the soaking. The $AgNO_3$ solution deposited silver particles, which scatter light effectively for OCT measurements, on the surface of the lens.

Excess $AgNO_3$ solution was removed by gently shaking the lens and touching the lens edge and front curve to dry tissue. The beaker of DI $H_2O$ was placed onto stir plate and stirring action was maintained. The lens was soaked in DI $H_2O$ for 30 seconds. Excess DI $H_2O$ was removed by gently shaking the lens and touching the lens edge and front curve to dry tissue. After every 10 lenses rinsed with the DI $H_2O$, the DI $H_2O$ was replaced. Twenty four more lenses were coated according to concentrations and soak times in Table 1 in preparation for measurement using OCT.

TABLE 1

Testing Parameters

| Group | Test | Lens | $AgNO_3$ Conc. (wt %) | Soaking Time (sec.) |
|---|---|---|---|---|
| 1 | 1 | 1 | 0.01 | 5 |
|   | 2 | 2 | 0.01 | 5 |
|   | 3 | 3 | 0.01 | 5 |
| 2 | 4 | 1 | 0.01 | 10 |
|   | 5 | 2 | 0.01 | 10 |

TABLE 1-continued

Testing Parameters

| Group | Test | Lens | AgNO₃ Conc. (wt %) | Soaking Time (sec.) |
|---|---|---|---|---|
|  | 6 | 3 | 0.01 | 10 |
| 3 | 7 | 1 | 0.01 | 15 |
|  | 8 | 2 | 0.01 | 15 |
|  | 9 | 3 | 0.01 | 15 |
| 4 | 10 | 1 | 0.01 | 20 |
|  | 11 | 2 | 0.01 | 20 |
|  | 12 | 3 | 0.01 | 20 |
| 5 | 13 | 1 | 0.01 | 30 |
|  | 14 | 2 | 0.01 | 30 |
|  | 15 | 3 | 0.01 | 30 |
| 6 | 16 | 1 | 0.02 | 5 |
|  | 17 | 2 | 0.02 | 5 |
|  | 18 | 3 | 0.02 | 5 |
| 7 | 19 | 1 | 0.02 | 10 |
|  | 20 | 2 | 0.02 | 10 |
|  | 21 | 3 | 0.02 | 10 |
| 8 | 22 | 1 | 0.02 | 15 |
|  | 23 | 2 | 0.02 | 15 |
|  | 24 | 3 | 0.02 | 15 |
| 9 | 25 | 1 | 0.02 | 20 |
|  | 26 | 2 | 0.02 | 20 |
|  | 27 | 3 | 0.02 | 20 |
| 10 | 28 | 1 | 0.02 | 30 |
|  | 29 | 2 | 0.02 | 30 |
|  | 30 | 3 | 0.02 | 30 |
| 11 | 31 | 1 | 0.04 | 5 |
|  | 32 | 2 | 0.04 | 5 |
|  | 33 | 3 | 0.04 | 5 |
| 12 | 34 | 1 | 0.04 | 10 |
|  | 35 | 2 | 0.04 | 10 |
|  | 36 | 3 | 0.04 | 10 |
| 13 | 37 | 1 | 0.04 | 15 |
|  | 38 | 2 | 0.04 | 15 |
|  | 39 | 3 | 0.04 | 15 |
| 14 | 40 | 1 | 0.04 | 20 |
|  | 41 | 2 | 0.04 | 20 |
|  | 42 | 3 | 0.04 | 20 |
| 15 | 43 | 1 | 0.04 | 30 |
|  | 44 | 2 | 0.04 | 30 |
|  | 45 | 3 | 0.04 | 30 |
| 16 | 46 | 1 | 0.08 | 5 |
|  | 47 | 2 | 0.08 | 5 |
|  | 48 | 3 | 0.08 | 5 |
| 17 | 49 | 1 | 0.08 | 10 |
|  | 50 | 2 | 0.08 | 10 |
|  | 51 | 3 | 0.08 | 10 |
| 18 | 52 | 1 | 0.08 | 15 |
|  | 53 | 2 | 0.08 | 15 |
|  | 54 | 3 | 0.08 | 15 |
| 19 | 55 | 1 | 0.08 | 20 |
|  | 56 | 2 | 0.08 | 20 |
|  | 57 | 3 | 0.08 | 20 |
| 20 | 58 | 1 | 0.08 | 30 |
|  | 59 | 2 | 0.08 | 30 |
|  | 60 | 3 | 0.08 | 30 |
| 21 | 61 | 1 | 0.16 | 5 |
|  | 62 | 2 | 0.16 | 5 |
|  | 63 | 3 | 0.16 | 5 |
| 22 | 64 | 1 | 0.16 | 10 |
|  | 65 | 2 | 0.16 | 10 |
|  | 66 | 3 | 0.16 | 10 |
| 23 | 67 | 1 | 0.16 | 15 |
|  | 68 | 2 | 0.16 | 15 |
|  | 69 | 3 | 0.16 | 15 |
| 24 | 70 | 1 | 0.16 | 20 |
|  | 71 | 2 | 0.16 | 20 |
|  | 72 | 3 | 0.16 | 20 |
| 25 | 73 | 1 | 0.16 | 30 |
|  | 74 | 2 | 0.16 | 30 |
|  | 75 | 3 | 0.16 | 30 |

Diameter, center thickness, and base curve were measured for each lens of the twenty five lenses prior to and after coating to determine if the coating procedure affected the basic lens geometry. The coating procedure was found to not affect the basic lens geometry.

After the lenses were coated, they were allowed to settle for one day prior to measurement on the Santec SS-OCT (available from Santec, Ohkusa, Japan). Both non-averaged and 10 frame average images were acquired for each lens. A targeted group of lenses with the best coatings were selected for Santec Lens Profile measurements (using custom analysis test script software in Matlab R2009b to quantify the average signal intensity of each coated lens and Minitab v15.1), which images a lens profiles at 10 degree intervals. This allowed for the inspection of coating consistency over a large portion of the lens surface.

Figure 4:
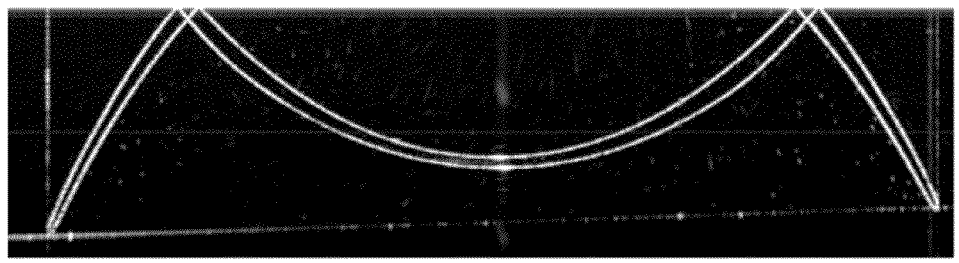
FIG. 4 shows an OCT image of a contact lens coated with a silver nitrate solution.
Figure 5:
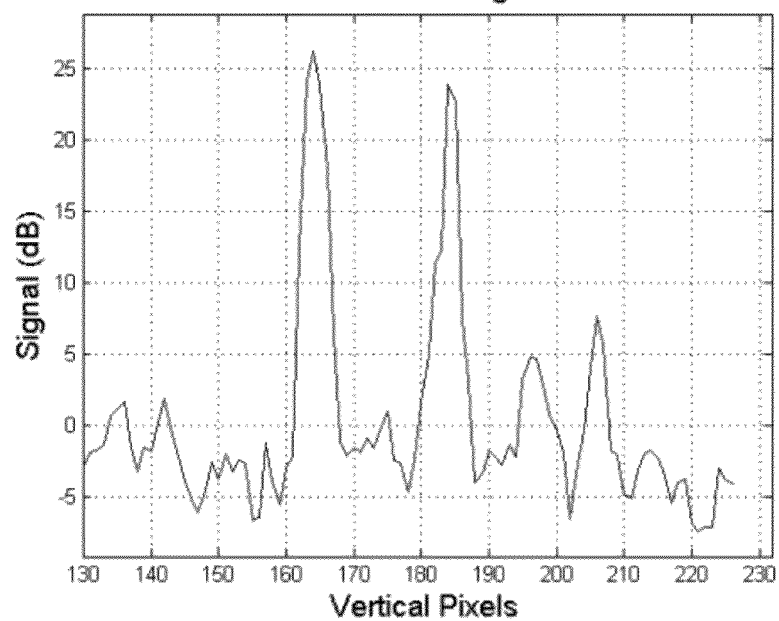
FIG. 5 shows a line profile through the contact lens imaged in FIG. 4.
Figure 6:
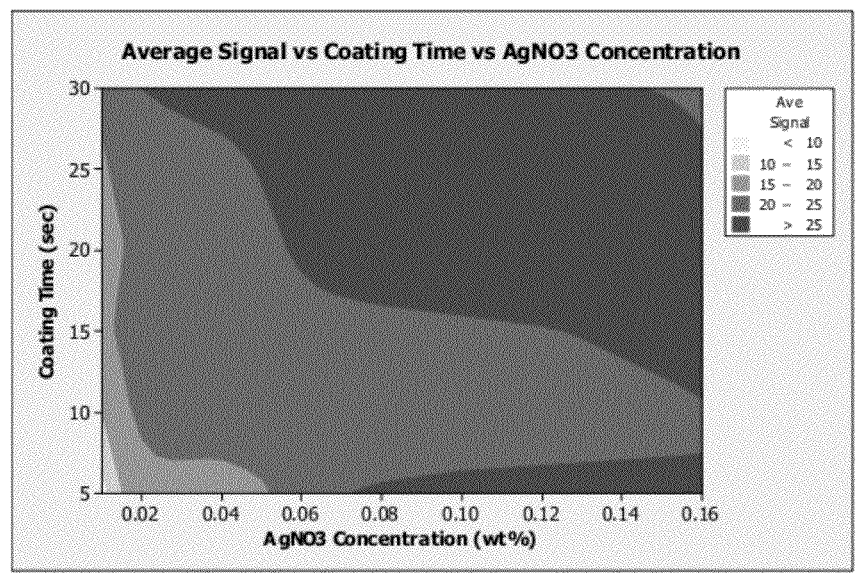
FIG. 6 shows a plot of average signal strength for the various silver nitrate concentrations and coating times.

The average signal intensity was found by focusing on a section of the lens just outside of the center (see FIG. 4). This encompassed 225 vertical pixel columns across the lens profile. The two highest intensity points per vertical pixel profile were found (see FIG. 5). To exclude adjacent pixels around the highest intensity, a +/−5 pixel mask was placed around the maximum pixel intensity for the second peak finding. The average of the two peaks of all 225 vertical profiles was calculated for each lens which resulted in the "average signal intensity" metric. The results for the various concentrations and coating times are shown in FIG. 6.

As shown above, the best signal in the study was found using higher concentrations and longer soaking times. The overall process window measured in this study shows relatively small changes in lens edge signal over large concentration and time changes. For example, doubling the $AgNO_3$ concentration from 0.08 wt % to 0.16 wt % resulted in only a small increase in signal. This results in a robust coating technique that will have low sensitivity to slight changes in process conditions.

Figure 7:
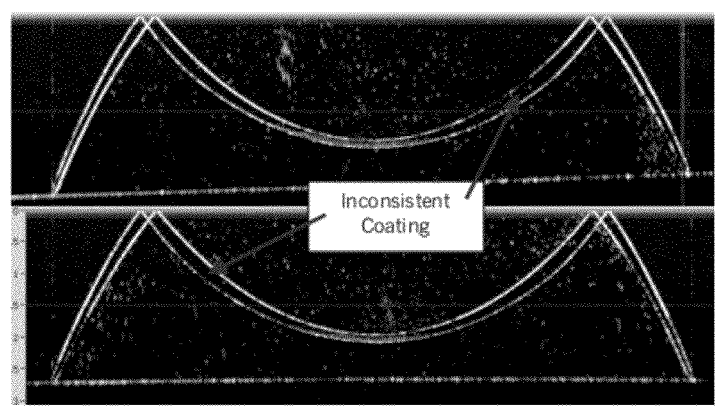
FIG. 7 shows a pair of OCT images of contact lenses coated with a solution comprising 0.08 wt % of silver nitrate.
Figure 8:
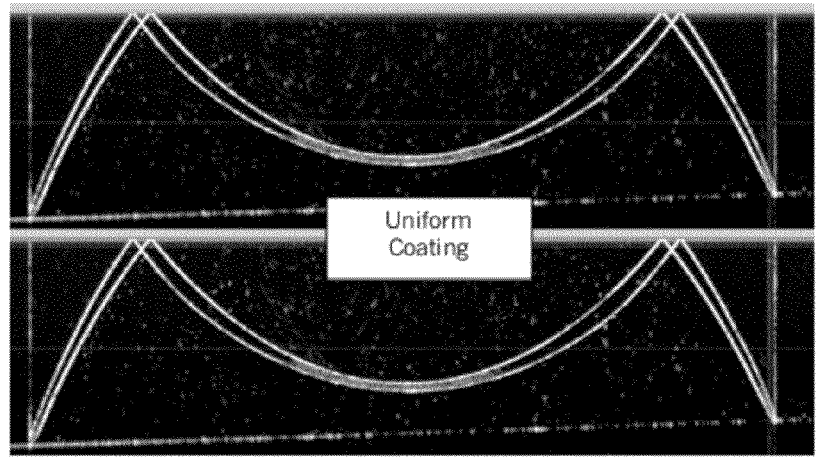
FIG. 8 shows a pair of OCT images of contact lenses coated with a solution comprising 0.16 wt % of silver nitrate.

To help identify the best coating conditions, a targeted sampling of the 0.08 wt % and 0.16 wt % concentrations were selected to be measured for lens thickness profile measurements on the Santec OCT. The meridian profile images, taken every 10 degrees, allowed for the inspection of coating consistency. The lenses coated with 0.08 wt % $AgNO_3$ had less consistent coatings; whereas the lenses coated with 0.16 wt % $AgNO_3$ had very similar coatings on all meridians (see FIGS. 7 and 8).

The 0.16 wt % $AgNO_3$ concentration and 10 second coating time procedure was selected as the optimized coating since it yielded the highest signal intensity and most uniform coating with a fast dip coating time.

Figure 9:
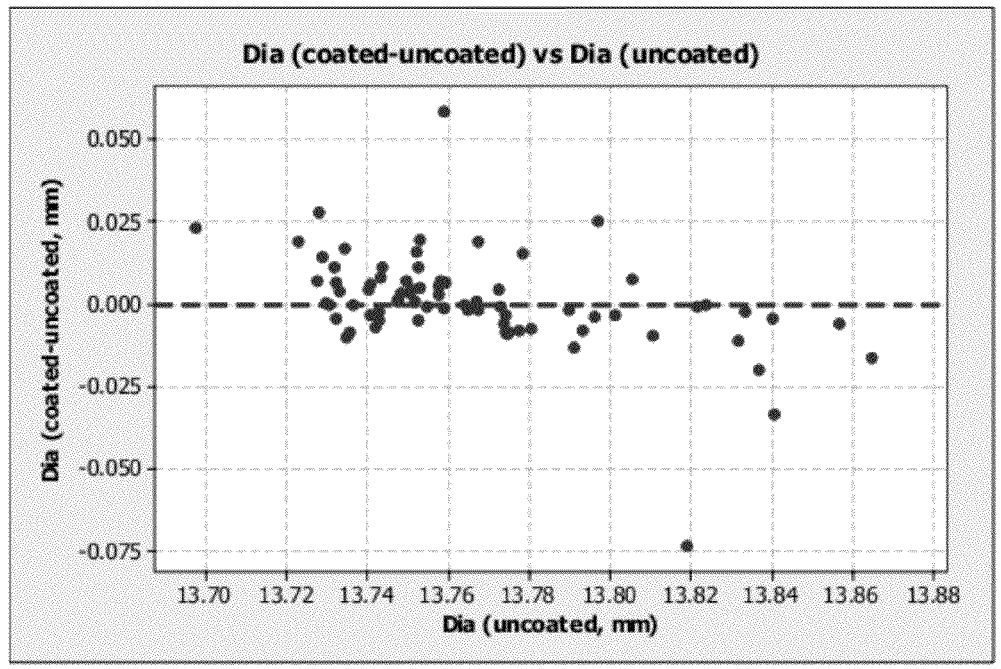
FIGS. 9-12 show various scatterplots of contact lens properties when coated with a dye and when not coated with the dye.

As shown in the following plots (FIG. 9), the diameter, center thickness, and base curve were unaffected by the $AgNO_3$ coating procedure. One of the main applications for the Santec OCT system is the lens thickness measurement. Therefore, it appears that the coating procedure will not affect the measured thickness profiles of the lenses as measured by the Santec OCT.

Figure 10:
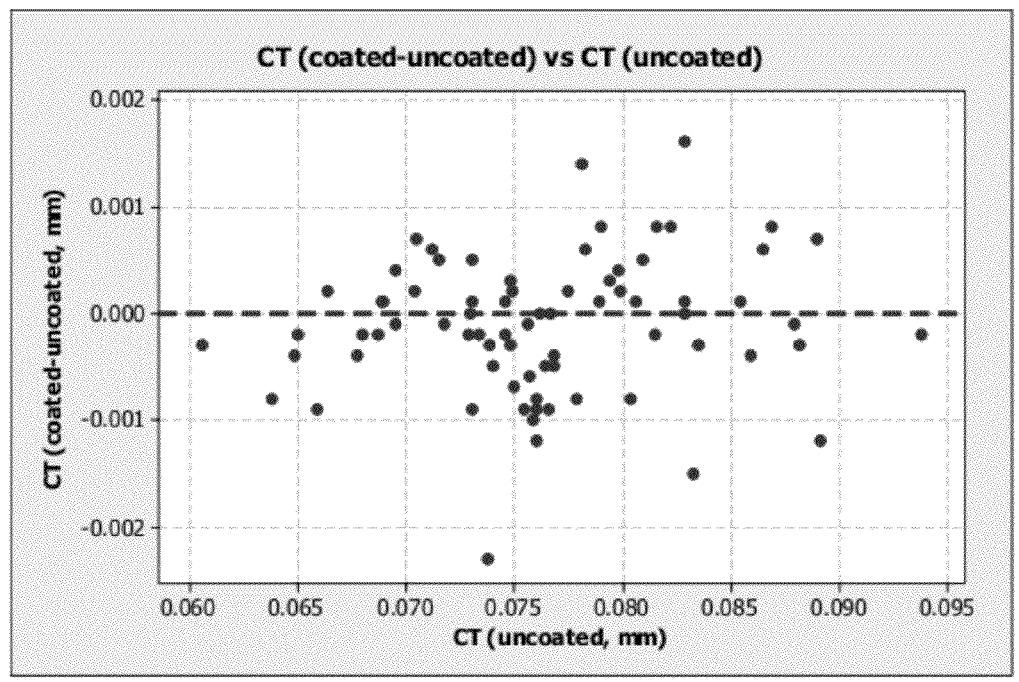
Figure 11:
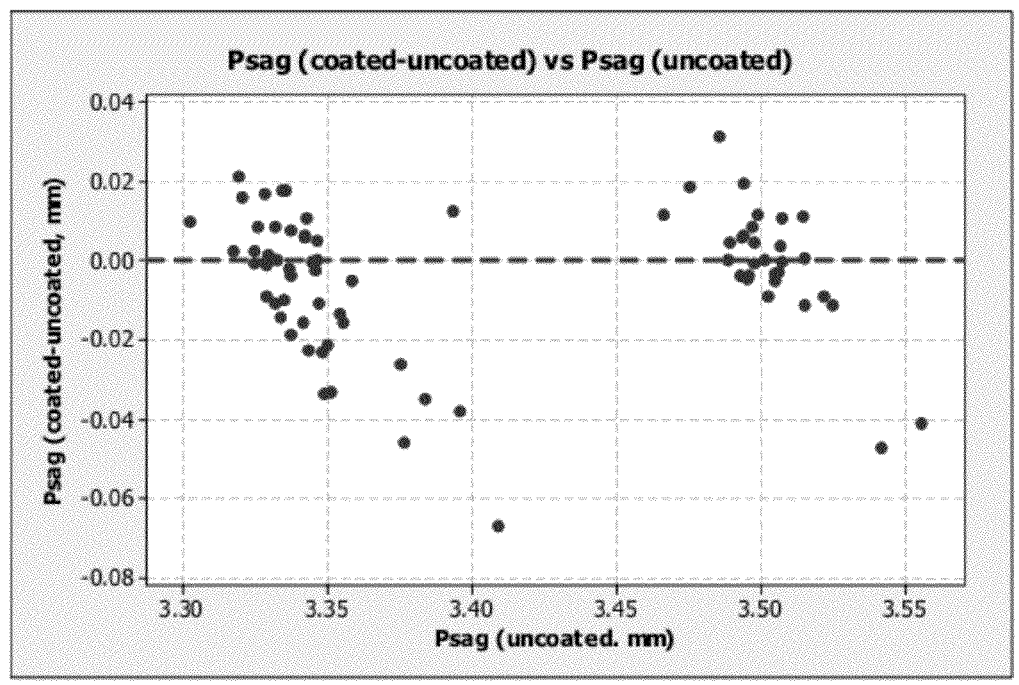

A paired T-test (95% CI) was completed to verify that the before and after coating dimensions were not statistically different. The diameter and CT measurements (see FIG. 10) were shown to not to be statistically different. The t-test indicated that the PSag before and after coating might be statistically different (p-value=0.047). The difference in the overall mean PSag before and after coating was ~4 µm, which is practically insignificant. However, a detailed examination of the PSag data revealed some potential anisotropic shrinkage of the lenses after coating (see FIG. 11). A trend is evident within lenses of the same target base curve.

Figure 12:
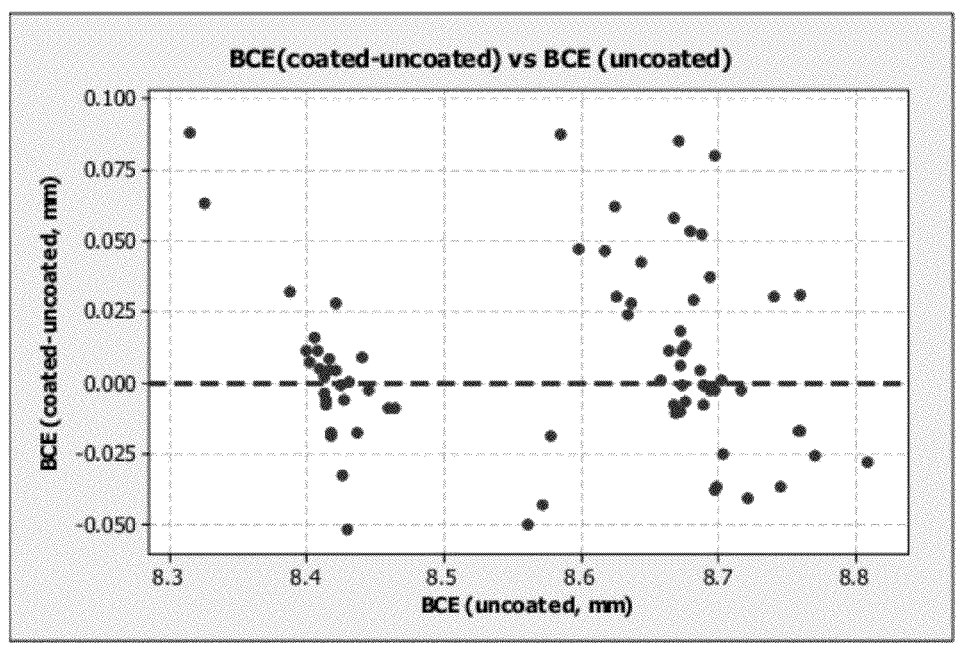

The BCE showed similar results to the PSag (see FIG. 12), indicating that changes in PSag (not in diameter) were driving the differences in BCE. The difference in the overall means between the groups was ~7 μm, which is practically insignificant.

Although the lens thickness profiles seemed to be unaffected by the lens coating procedure (CT unaffected by coating), other measurements from the Santec OCT (e.g., BCE determination) could be impacted by slight changes in the PSag during the coating process.

While the invention has been described with reference to preferred and example embodiments, it will be understood by those skilled in the art that a variety of modifications, additions and deletions are within the scope of the invention, as defined by the following claims.

What is claimed:

1. A method for imaging an ocular device comprising:
   a. applying a scattering agent to the ocular device, wherein the scattering agent comprises a pigment;
   b. rinsing the device;
   c. submerging the device in a solution of water, saline, or a buffered solution; and
   d. imaging the ocular device using optical coherence tomography (OCT).

2. The method of claim 1, wherein the pigment comprises Green $Cr_2O_3$, Yellow Iron Oxide, or any combination thereof.

3. The method of claim 2, wherein the ocular device is a contact lens.

4. The method of claim 2, wherein the ocular device is an intraocular lens.

5. The method of claim 1, wherein the pigment comprises a water-insoluble salt that forms in situ on the surface of the device, throughout the device, or a combination thereof.

6. The method of claim 5, wherein the water-insoluble salt comprises a silver salt.

7. The method of claim 3, wherein the ocular device is a contact lens.

8. The method of claim 1, wherein step (a) comprises submerging the ocular device in a solution comprising the scattering agent.

9. The method of claim 8, wherein the ocular device is imaged in a solution of the scattering agent.

10. The method of claim 1, wherein the ocular device is imaged in a solution of the scattering agent.

11. The method of claim 1, wherein the device is imaged by a Frequency Domain OCT, Fourier-domain OCT (FDOCT), complex Fourier OCT, Optical Frequency-domain imaging, or swept-source OCT.

12. The method of claim 1, wherein the ocular device is a contact lens.

13. The method of claim 1, wherein the ocular device is an intraocular lens.

* * * * *